United States Patent [19]

Helsley et al.

[11] 4,031,221

[45] June 21, 1977

[54] METHOD OF TREATING PAIN AND HYPERTENSION

[75] Inventors: Grover C. Helsley, Pottersville; Joseph Strupczewski, Piscataway, both of N.J.

[73] Assignee: American Hoechst Corporation, Bridgewater, N.J.

[22] Filed: June 19, 1975

[21] Appl. No.: 588,135

Related U.S. Application Data

[62] Division of Ser. No. 480,205, June 17, 1974, abandoned.

[52] U.S. Cl. .............................. 424/267; 424/244; 424/274

[51] Int. Cl.$^2$ ................ A61K 31/33; A61K 31/40; A61K 31/445

[58] Field of Search ........................... 424/267, 274

[56] References Cited

UNITED STATES PATENTS 3,642,803  9/1972  Welstead ..................... 260/293.61

Primary Examiner—Stanley J. Friedman
Attorney, Agent, or Firm—Curtis, Morris & Safford

[57] ABSTRACT

3-[2-(Phenyloxycycloazalkyl)ethyl]indoles possessing antihypertensive, analgesic, and tranquilizing properties and process for their preparation are described.

36 Claims, 1 Drawing Figure

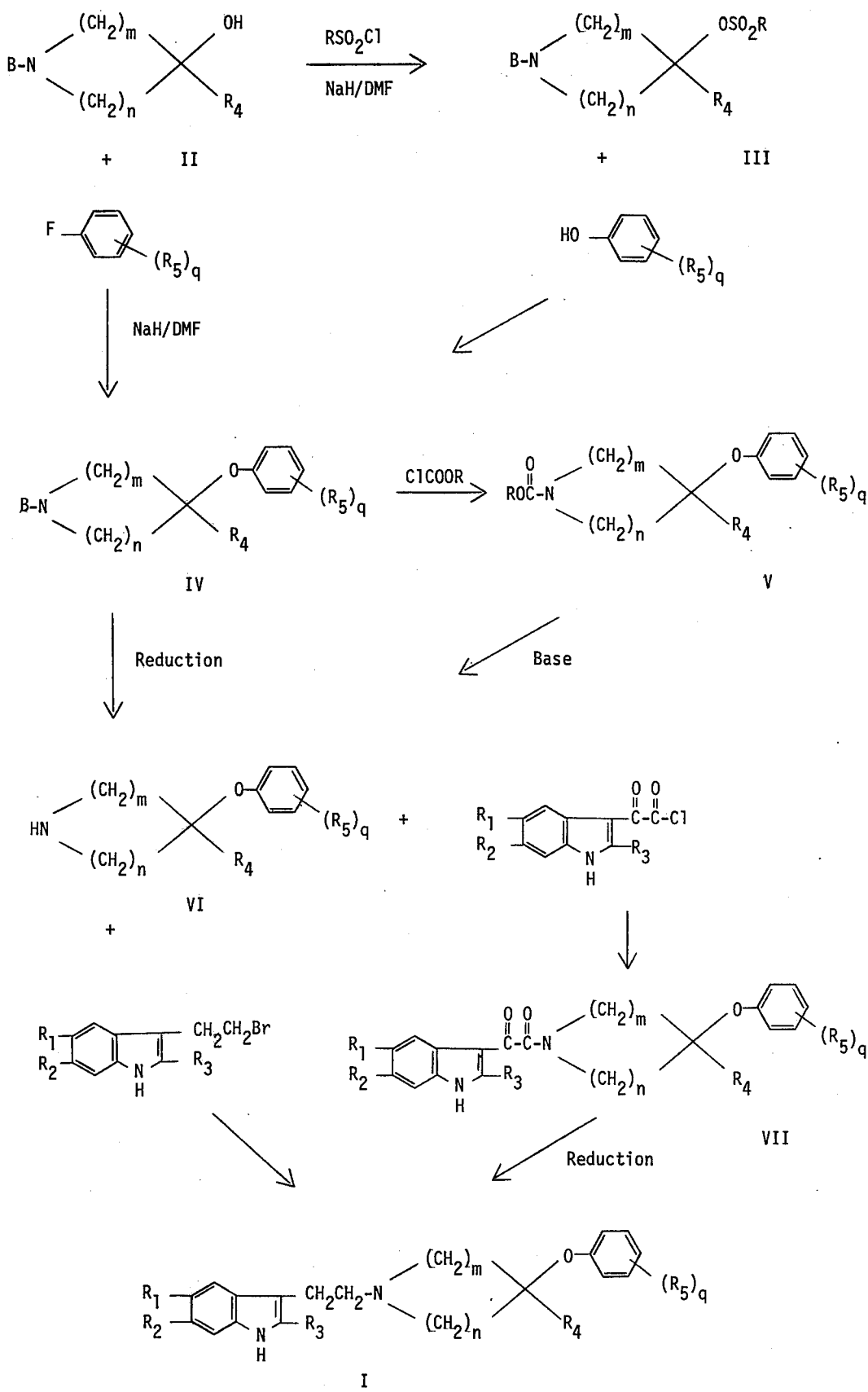

METHOD OF TREATING PAIN AND HYPERTENSION

This is a division of application Ser. No. 480,205 filed June 17, 1974, now abandoned.

This invention relates to 3-[2-phenyloxycycloazalkyl-)ethyl]indoles possessing antihypertensive, analgesic, and tranquilizing properties and to a process for their preparation.

To the best of our knowledge, the compounds of the present invention have not heretofore been described. Indoles exhibiting action on the cardiovascular system are mentioned in U.S. Pat. No. 3,527,761 (1970). U.S. Pat. No. 3,188,313 (1965) describes 1-(1,2, and 3-indolyl)-lower piperazine derivatives as having important biological activity.

The compounds of the invention have the formula:

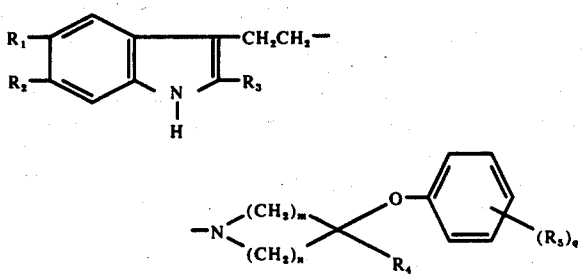

in which $R_1$ and $R_2$ are hydrogen, halogen, alkyl of from 1 to 3 carbon atoms, alkoxy of 1 to 2 carbon atoms or phenalkoxy of 7 to 9 carbon atoms; $R_3$ is hydrogen or alkyl of from 1 to 3 carbon atoms; $R_4$ is hydrogen or phenyl; $R_5$ is halogen, alkyl of from 1 to 4 carbon atoms, alkoxy of from 1 to 3 carbon atoms, nitro or trifluoromethyl; $m$ is an integer from 1 to 3; $n$ is 1 or 2; and $q$ is 0, 1 or 2; and the physiologically tolerable acid addition salts thereof. The compounds that are preferred are those in which $R_1$ and $R_2$ are hydrogen, bromine, methoxy or benzyloxy, $R_3$ is hydrogen or methyl, $R_5$ is methyl, fluorine, chlorine, bromine or trifluoromethyl, $m$ and $n$ are both 2, and $q$ is 0 or 1.

The compounds of the invention are prepared by any of several multi-step sequences of reactions as described below and illustrated in the attached drawing, in which R represents alkyl or aryl, B represents benzyl or benzhydryl, and $R_{1-5}$, $m$, $n$ and $q$ are as defined above.

In one embodiment of the method of the invention, a compound of formula II, such as a benzylpiperidinol, is reacted with an alkyl-or arylthionylchloride to form the corresponding N-benzyl-alkyl- or arylthionylpiperidine compound of Formula III. This compound is allowed to react with a phenol in a basic medium to produce an N-benzyl- or N-benzhydrylphenoxypiperidine of Formula IV. One preferred method utilizes sodium hydride in dimethylformamide as the basic medium, and the reaction spans 48 hours at a temperature of about 60° C. A compound of Formula IV is reduced in a suitable medium to give a compound of formula VI. A compound of Formula VII is produced by the addition of an indole-3-glyoxyloychloride in the presence of a suitable solvent, at a temperature of from 0°-40° C. and in a period of from a few minutes to 30 hours. An acid scavenger may be added to the reaction mixture to take up the hydrogen chloride liberated by the reaction. In a preferred method, chloroform is the solvent and potassium carbonate is the acid scavenger. A compound of Formula VII can be reduced by methods known to the art to give a corresponding compound of the invention represented by Formula I. A preferred method utilizes an alkali metal hydride such as lithium aluminum hydride in an organic solvent such as tetrahydrofuran under an inert atmosphere such as nitrogen.

In a second embodiment, a compound of Formula II is reacted with a fluorobenzene in a suitable organic solvent such as dimethylformamide for 30 minutes to 72 hours at a temperature of from 25°-125° C., to give a compound of Formula IV. When $R_5$ does not represent chloro or bromo, reduction can be effected by methods known to the art to give a compound of Formula VI. A preferred method is subjecting the compound to hydrogenolysis in the presence of a noble metal, such as palladium, on charcoal catalyst at a temperature of about 50° C. until the theoretical quantity of hydrogen is taken up. A compound of the invention of Formula I is prepared from a compound of Formula VI as described earlier.

In a third embodiment, a compound of Formula IV is prepared as described in the second embodiment when $R_5$ represents chloro or bromo, a compound of Formula IV is reacted with an alkyl or aryl chloroformate in a suitable solvent for from 2 hours to 24 hours to produce a compound of Formula V. A preferred method is refluxing the reactants in benzene or toluene for 18 hours. The secondary amine of Formula VI is obtained by dissolving a compound of Formula V in a suitable solvent such as ethanol, adding an aqueous alkaline solution such as 45% potassium hydroxide and refluxing the solution for from a few minutes to 18 hours, preferably about 12 hours, under an inert atmosphere such as nitrogen. A compound of the invention of Formula I is prepared from a compound of Formula VI as described earlier.

In a fourth embodiment, a compound of Formula VI, prepared as previously described in the second embodiment, is reacted with a 3-(2-bromoethyl)indole in a suitable solvent with an acid scavenger at a temperature of from 15°-40° C. for from 1 hour to 24 hours to give a compound of the invention of Formula I. A preferred method utilizes dimethylformamide as the solvent, triethylamine as the acid scavenger. The reaction takes place overnight at ambient temperature.

In a still further embodiment, a compound of Formula VI, prepared as described above is reacted with 3-(2-bromoethyl)indole in a suitable solvent, with an acid scavenger at a temperature of from 20° to 83° C. for from 30 minutes to 24 hours, to give a compound of the invention of Formula I. In a preferred method, the reaction medium is refluxing isopropanol, the acid scavenger is potassium carbonate and the reaction time is about 22 hours.

The compounds of the invention are useful as antihypertensive agents due to their ability to depress blood pressure in mammals. Antihypertensive activity was measured in the spontaneous hypertensive rat by the indirect tail cuff method described in A. Schwartz, Ed., *Methods in Pharmacology*, Vol. I, p. 135, Appleton-Century-Crofts, New York, New York, 1971. In this procedure, a group of 5 animals were dosed orally with 100 milligrams of the drug per kilogram of body weight in relation to a control group of the same number. The anti-hypertensive activity in this test of some of the compounds of the invention is illustrated in Table I.

Table I

| Compound | Day 1 mm Hg | Day 3 mm Hg |
|---|---|---|
| 3-{2-[4-(p-Tolyloxy)piperidyl]ethyl}indole | −48.2 | −57.0 |
| 3-{2-[4-(p-Bromophenoxy)piperidyl[ethyl}indole | −24.2 | −58.8 |
| 5,6-Dimethoxy-2-methyl-3-{2-[4-(p-trifluoromethylphenoxy)piperidyl]ethyl}indole | −24.2 | −57.8 |
| 3-{2-[4-(p-Fluorophenoxy)piperidyl]ethyl}indole | −49.8 | −55.0 |
| 3-{2-[4-(p-Chlorophenoxy)piperidyl]ethyl}indole | −47.2 | −54.2 |

The compounds of the invention are also useful as analgesic agents due to their ability to alleviate pain in mammals. The activity of the compounds is demonstrated in the 2-phenyl-1,4-benzoquinone-induced writhing test in mice, a standard assay for analgesia [Proc. Soc. Exptl. Biol. Med., 95, 729 (1957)]. For example, at doses of 5.9, 18.5, 21, 25, and 45 mg./kg. of body weight, 3-{2-[4-(p-bromophenoxy)piperidyl]-ethyl}indole, 3-{2-[4-(m-tolyloxy)piperidyl]ethyl}indole, 3-[2-(4-phenoxypiperidyl)ethyl]indole, 3-{2-[4-(p-tolyoxy)piperidyl]ethyl}indole, 3-{2-[4-(p-trifluoromethylphenoxy)piperidyl]-ethyl}indole, respectively exhibit an approximately 50% inhibition of writhing.

The compounds of the invention are also useful as tranquilizers due to their depressant action on the central nervous system of mammals. This activity is demonstrated in the mouse observation procedure, a standard assay for central nervous system depressants [Psychopharmacologia, 9, 259 (1966)]. Thus, for example, the minimum effective dose (MED) at which 3-{2-[4-(p-fluorophenoxy)piperidyl]ethyl}indole displays significant effects on behavior and reflex depression together with muscle relaxation is 25 mg./kg. of body weight. Similarly, MED's of other compounds are:

|  | MED mg/kg. |
|---|---|
| 3-[2-(4-Phenoxypiperidyl)ethyl]indole | 37.5 |
| 3-{2-[4-(p-Trifluoromethylphenoxy)piperidyl]ethyl}indole | 37.5 |

Examples of other compounds of the invention include: 3-{2-[4-(p-Nitrophenoxy)hexamethyleneiminyl]ethyl}indole 3-{2-[3-(3,5-Dichlorophenoxy)hexamethyleneiminyl]ethyl}indole; 3-{2-[3-(o-Fluorophenoxy)pyrrolidinyl]ethyl}indole; 2-Ethyl-6-ethoxy-3-[2-(4-phenoxypiperidyl)ethyl]ethyl]indole; 3-[2-(4-Phenyl-4-phenoxypiperidyl)ethyl]indole; 5-Phenethoxy-3-{2-[4-(p-trifluoromethylphenoxy)piperidyl]-ethyl}indole; 5,6-Dimethoxy-2-methyl-3-{2-[4-(p-trifluoromethylphenoxy)-piperidyl]ethyl}indole; and, 5-chloro-3-{2-[4-(p-fluorophenoxy)piperidyl]ethyl}indole.

The compounds of the present invention may be administered to a patient by any convenient route such as orally, intramuscularly, intravenously, subcutaneously, or intraperitoneally. The preferred route of administration is oral, for example, with an inert diluent or with an edible carrier or in gelatin capsules or tablets.

For the purpose of oral therapeutic administration, the active compounds of this invention may be incorporated with excipients and used in the form of tablets, troches, capsules, elixirs, suspensions, syrups, wafers, chewing gum, and the like. These preparations should contain at least 0.5% of active compound, but may be varied depending upon the particular form and may conveniently be between 7% to about 70% by weight of the unit. The amount of active compound in such compositions is such that a suitable dosage will be obtained. Preferred compositions and preparations according to the present invention are prepared so that an oral dosage unit form contains between 10 and 200 milligrams of active compound.

The tablets, pills, capsules, troches, and the like may also contain the following ingredients: a binder such as gum tragacanth or gelatin; an excipient such as starch or lactose, a disintegrating agent such as alginic acid, potato starch and the like; a lubricant such as magnesium stearate; and a sweetening agent such as sucrose or saccharin may be added or a flavoring agent as peppermint, methyl salicylate, or orange flavoring. When the dosage unit form is a capsule, it may contain, in addition to materials of the above type, a liquid carrier such as a fatty oil. Other dosage unit forms may contain other various materials which modify the physical form of the dosage unit, for example, as coatings. Thus, tablets or pills may be coated with sugar, shellac, or both. A syrup may contain, in addition to the active compounds sucrose as a sweetening agent, and certain preservatives, dyes and colorings, and flavors. Materials used in preparing these various compositions must be pharmaceutically pure and non-toxic in the amounts utilized.

Acids useful for preparing the physiologically tolerable acid addition salts of the invention include inorganic acids such as hydrochloric, hydrobromic, sulfuric, nitric, phosphoric and perchloric acids, as well as organic acids such as oxalic, tartaric, citric, acetic, succinic, maleic and ethane disulfonic acids.

EXAMPLE 1 a. 21.0 g of 1-benzyl-3-piperidinol in 700 ml. of dimethylformamide are added dropwise to a stirred suspension of 8.0 g of a 50% oil dispersion of sodium hydride in 220 ml. of dimethylformamide at 60°–70° C. Heating and stirring is continued until no more hydrogen gas is liberated and then a solution of 24.0 g of p-fluorotoluene in 70 ml. of dimethylformamide is added. The reaction mixture is stirred at a temperature of 98° C. for 87 hours, allowed to cool and then poured into 600 ml. of water. The aqueous solution is extracted with benzene, the benzene extracts are washed with water, dried, and the benzene is removed leaving a brown oil. The oil is heated under a high vacuum for 1 hour and then fractionally distilled under reduced pressure. The fraction which boils at 163° C/0.2/mm is 1-benzyl-3-(p-tolyloxy)piperidine.

b. A solution of 2.9 g of 1-benzyl-3-(p-tolyloxy) piperidine in 30 ml. of 95% ethanol is added to 0.42 g of 10% Pd-C, and hydrogenated at about 50° C. for 3 hours. Then the reaction mixture is cooled to ambient temperature, the 10% Pd-C is filtered off, and the ethanol is removed leaving a yellow oil of 3-(p-tolyloxy)-piperidine.

c. A solution of 7.0 g of 3-(2-bromoethyl)indole, 3.2 g of triethylamine and 5.4 g of 3-(p-tolyloxy)piperidine in 130 ml. of dimethylformamide is stirred overnight at ambient temperature. Then 260 ml. of water are added dropwise to the stirring solution, causing a yellow oil to separate, the aqueous solution is decanted from the oil, the oil is taken up in ether, the ether is washed with water, and dried. The ether is removed, leaving an orange oil. The oil is dissolved in isopropanol and a solution of anhydrous oxalic acid in an isopropanol and ether mixture is added slowly to give a white oxalate salt. The salt is recrystallized from ethanol to give a microcrystalline solid of 3-{2-[3-(p-tolyloxy)-piperidyl]-ethyl}indole oxalate, m.p. 134°–136° C.

Analysis: Calculated for $C_{22}H_{26}N_2O \cdot (COOH)_2$: 67.83% C; 6.65% H; 6.60% N. Found: 67.74% C; 6.65% H; 6.53% N.

EXAMPLE 2 a. By following the manipulative procedure described in Example 1(a), 21.0 g of 1-benzyl-4-piperidinol and 24.0 g of o-fluorotoluene produces a yellow oil fraction which boils at 161°–163° C., 0.09 mm. This oil solidifies slowly upon standing and is recrystallized from petroleum ether (b.p. 30°–60°) to give white crystals of 1-benzyl-4-(o-tolyloxy) piperidine.

b. By following the manipulative procedure described in Example 1(b), a solution of 8.3 g of 1-benzyl-4-(o-tolyloxy)piperidine in 100 ml. of ethanol produces a colorless oil of 4-(o-tolyloxy)piperidine.

c. A solution of 8.0 g of 4-(o-tolyloxy)piperidine in 45 ml. of chloroform is added to a stirred solution of 10.1 g of potassium carbonate in 45 ml. of water. The mixture is stirred vigorously and 8.3 g of indole-3-glyoxyloyl chloride are added portionwise. The mixture is stirred at ambient temperature for 23 hours, effecting a white solid. The solid is collected, washed well with ether, and dried. The solid is recrystallized from a methanol and water mixture to give white needles, m.p. 171°–173° C., of 1-(indol-3-ylglyoxyloyl)-4-(o-tolyloxy)piperidine.

d. A solution of 8.7 g of 1-(indol-3-ylglyoxyloyl)-4-(o-tolyloxy)piperidine in 80 ml. of tetrahydrofuran is added dropwise to a stirred suspension of 4.2 g of lithium aluminum hydride in 120 ml. of tetrahydrofuran. After addition is complete, the mixture is stirred and refluxed for 3 hours under nitrogen. The reaction mixture is then cooled and excess hydride is carefully destroyed with water. The mixture is filtered, the filter cake washed with tetrahydrofuran, and the tetrahydrofuran is removed under reduced pressure to give an oil. The oil is evacuated at about 3 mm. overnight, and then rubbed with a glass rod in the presence of hexane to give a white solid. the solid is recrystallized from a benzene and hexane mixture (charcoal treatment) to give off-white crystals. These crystals are recrystallized from an isopropanol and water mixture to give white flakes of 3-{2-[4-(o-tolyloxy)piperidyl]ethyl}indole, m.p. 88°–90° C.

Analysis: Calculated for $C_{22}H_{26}N_2O$: 79.00% C; 7.83% H; 8.37% N. Found: 78.97% C; 7.82% H; 8.26% N.

EXAMPLE 3 a. By following the manipulative procedure described in Example 1(a), 24.0 g of 1-benzyl-4-piperidinol and 24.0 g of m-fluorotoluene produces a brown oil. The fraction which boils at 159°–163° C./0.05mm, is 1-benzyl-4-(m-tolyloxy)piperidine.

b. By following the manipulative procedure described in Example 1(b), a solution of 16.6 g of 1-benzyl-4-(m-tolyloxy)piperidine in 105 ml. of ethanol produces a clear oil of 4-(m-tolyloxy)piperidine. The oil is dissolved in 150 ml. of ether, and 50 ml. of a saturated ethereal-HCl solution is slowly added. The salt precipitates out of solution, is collected, and dried. The salt is recrystallized from an ethanol and ether mixture to give white needles of the piperidine hydrochloride.

c. 8.3 g of indole-3-glyoxyloyl chloride are added to a stirred mixture of 10.1 g of potassium carbonate in 45 ml. of water and 9.5 g of 4-(m-tolyloxy)piperidine in 45 ml. of chloroform. The mixture is stirred overnight and the chloroform layer is evaporated under reduced pressure leaving a yellow oil. The oil is rubbed with a glass rod in the presence of ether to give a white solid. The solid is collected, washed with ether, and dried. The solid is recrystallized from an ethyl acetate and cyclohexane mixture to give white crystals, m.p. 149°–151° C., of 1-(indol-3-ylglyoxyloyl)-4-(m-tolyloxy)piperidine.

d. A solution of 10.0 of 1-(indol-3ylglyoxyloyl)-4-(m-tolyloxy)piperidine in 205 ml. of tetrahydrofuran is added dropwise to a stirred suspension of 4.8 g of lithium aluminum hydride in 140 ml. of tetrahydrofuran. After the addition is complete, the mixture is stirred and refluxed for 3 hours under nitrogen, cooled, and the excess hydride is carefully destroyed with water. The inorganic precipitate is filtered off and washed with tetrahydrofuran. The filtrate is concentrated, under reduced pressure, to a clear oil which crystallizes to a white solid. The solid is recrystallized from acetonitrile to give white needles of 3-{2-[4-(m-tolyloxy)piperidyl]ethyl}indole, m.p. 145°–146° C.

Analysis: Calculated for $C_{22}H_{26}N_2O$: 79.00% C; 7.83% H; 8.37% N. Found: 78.92% C; 8.01% H; 8.34% N.

EXAMPLE 4 a. By following the manipulative procedures described in Example 1(a) and (b), 24.0 g of 1-benzyl-4-piperidinol and 24.0 g of p-fluorotoluene produces an oil of 4-(p-tolyloxy)piperidine.

b. A solution of 4.9 g of 4-(p-tolyloxy)piperidine in 26 ml. of chloroform is added to a stirred solution of 6.4 g of potassium carbonate in 26 ml. of water. The mixture is stirred vigorously and 5.1 g of indole-3-glyoxyloyl chloride are added portionwise. After stirring at ambient temperature for 3 hours, 100 ml. of ether are added to effect a white solid. The mixture is permitted to stir for an additional 30 minutes and the solid is collected, washed with ether and dried. The solid is recrystallized from methanol to give white needles, m.p. 209°–211° C., of 1-(indol-3-ylglyoxyloyl)-4-(p-tolyloxy)piperidine.

c. A suspension of 4.0 g of 1-(indol-3-ylglyoxyloyl)-4-(p-tolyloxy)piperidine in 40 ml. of tetrahydrofuran is added dropwise to a stirred suspension of 2.1 g of lithium aluminum hydride in 60 ml. of tetrahydrofuran. After addition is complete the mixture is stirred and refluxed for 3 hours under nitrogen. After cooling, the excess hydride is carefully destroyed with water. The mixture is filtered, the filter cake is washed with tetrahydrofuran, and the filtrate is concentrated to a colorless oil under reduced pressure. The oil is kept under vacuum for 24 hours and then permitted to stand for several days. The oil slowly solidifies to a white solid. The solid is collected, washed with petroleum ether (b.p. 30°–60°) and recrystallized from an ethanol and water mixture to give white needles of 3-{2-[4-(p-tolyloxy)piperidyl]ethyl}indole, m.p. 115°–117° C.

Analysis Calculated for $C_{22}H_{26}N_2O$: 79.00% C; 7.84% H; 8.38% N. Found: 79.10% C; 7.89% H/ 8.35% N.

EXAMPLE 5 a. A solution of 21.6 g of 1-benzyl-4-piperidinol in 75ml. of dimethylformamide is added slowly to a stirred suspension of 8.7 g of a 50% oil dispersion of sodium hydride in 225 ml. of dimethylformamide at 60°–70° C. After addition is complete stirring and heating are continued until no more hydrogen gas is liberated. A solution of 19.6 g of 1-chloro-4-fluorobenzene in 75 ml. of dimethylformamide is added, and the solution is permitted to stir at 65°–70° C. for 16 hours. After cooling to ambient temperature, the solution is poured into 600 ml. of water, the aqueous solution is extracted with benzene, the benzene extracts are dried, and the benzene is removed under reduced pressure, leaving a yellow oil of 1-benzyl-4-(p-chlorophenoxy)-piperidine.

b. 12.1 ml. of ethylchloroformate are added to a solution of 19.4 g of 1-benzyl-4-(p-chlorophenoxy)-piperidine in 220 ml. of benzene and the solution is refluxed for 18 hours. The benzene and benzylchloride is removed under reduced pressure to give the N-ethoxycarbonylpiperidine as an uncrystallizable yellow oil. The N-ethoxycarbonylpiperidine is dissolved in 210 ml. of ethanol and 130 ml. of 45% aqueous potassium hydroxide are added. The solution is refluxed for 12 hours under nitrogen, cooled, most of the ethanol is removed under reduced pressure and the resultant oily dispersion is extracted with ether. The ether phase is extracted with 3 N hydrochloric acid, the acid extract is basified with 6N sodium hydroxide, and the basic solution is extracted with benzene. The benzene is dried and removed under reduced pressure to give a colorless oil. The oil is dissolved in 200 ml. of ether, the solution is cooled and stirred and 200 ml. of a saturated ethereal-HCl solution is slowly added. The salt forms and is collected. The salt is recrystallized from absolute ethanol to give 4-(p-chlorophenoxy)piperidine hydrochloride.

c. A solution of 5.4 g of 4-(p-chlorophenoxy)piperidine hydrochloride in 25 ml. of chloroform is added to a solution of 5.6 g of potassium carbonate in 25 ml. of water. The mixture is stirred vigorously and 4.6 g of indole-3-glyoxyloyl chloride are added portionwise. After addition is complete, a white solid forms. After the solid forms, the mixture is stirred an additional 25 minutes, the solid is collected, washed with ether, and dried. The solid is recrystallized from an ethanol and water mixture to give white needles, m.p. 199°–200° C., of 1-(indol-3-ylglyoxyloyl)-4-(p-chlorophenoxy)piperidine.

d. 60 ml. of a 1M solution of boron trihydride in tetrahydrofuran are added dropwise to a stirred solution of 7.0 g of 1-(indol-3-ylglyoxyloyl)-4-(p-chlorophenoxy)piperidine in 135 ml. of tetrahydrofuran under nitrogen. The solution is stirred at ambient temperature for 18 hours and the tetrahydrofuran is removed under reduced pressure to give a white boron complex. The complex is destroyed by refluxing in 135 ml. of methanol with a few drops of glacial acetic acid. After cooling, the methanol is removed under reduced pressure to give a yellow oil. The oil is dissolved in ether, the ether is washed with water, dried and removed under reduced pressure to give a yellow oil. After standing under vacuum for a week, the oil crystallizes to a yellow solid. The solid is recrystallized from toluene and then from an ethanol and water mixture to give white crystals of 3-{2-[4-(p-chlorophenoxy)-piperidyl]ethyl}indole, m.p. 132°–133° C.

Analysis: Calculated for $C_{21}H_{23}ClN_2O$: 71.07% C; 6.53% H, 7.90% N; 9.99% Cl. Found: 70.87% C; 6.71% H; 7.80% N; 10.01% Cl.

EXAMPLE 6 a. By following the manipulative procedures described in Example 1(a), (b) and (c), substituting 1-chloro-3-fluorobenzene for 1-chloro-4-fluorobenzene produces 1-(indol-3-ylglyoxyloyl)-4-(m-chlorophenoxy)piperidine, m.p. 145°–147° C.

b. 49 ml. of a 1M solution of boron trihydride in tetrahydrofuran are added dropwise to a stirred suspension of 5.3 g of 1-(indol-3-ylglyoxyloyl)-4-(m-chlorophenoxy)piperidine in 100 ml. of tetrahydrofuran under nitrogen. After an initial evolution of gas, the solution turns yellow and is stirred at ambient temperature for 13 hours. The tetrahydrofuran is removed under reduced pressure to give a solid white borane complex. The complex is destroyed by refluxing in 100 ml. of methanol with several drops of glacial acetic acid for one hour. After cooling, the methanol is removed under reduced pressure, leaving a yellow oil. The oil is evacuated at about 3 mm. for 72 hours and a gummy solid forms. The solid is recrystallized from acetonitrile and then from an ethanol and water mixture to give white microcrystals of 3-{2-[4-(m-chlorophenoxy)-piperidyl]ethyl}indole, m.p. 120°–123° C.

Analysis: Calculated for $C_{21}H_{23}ClN_2O$: 71.07% C; 6.53% H; 7.90% N; 9.99% Cl. Found: 71.20% C; 6.57% H; 7.88% N; 10.11% Cl.

EXAMPLE 7 a. By following the manipulative procedures described in Example 5(a) and (b), substituting 1-bromo-4-fluorobenzene for 1-chloro-4-fluorobenzene produces 4-(p-bromophenoxy)piperidine hydrochloride.

b. A mixture of 8.1 g of 4-(p-bromophenoxy)piperidine hydrochloride, 12.6 g of potassium carbonate and 60 ml. of isopropanol is stirred and refluxed for one hour. A solution of 6.5 g of 3-(2-bromoethyl)indole in 15 ml. of isopropanol is then added. Stirring and refluxing is continued for 22 hours, and the reaction mixture is filtered hot. A yellow oil separates in the cooled filtrate and the supernatant isopropanol is decanted from the oil. The isopropanol is diluted with ether, causing the unreacted 4-(p-bromophenoxy)piperidine to separate. After filtration, the isopropanol is removed under reduced pressure to give a yellow oil. The oil is permitted to stand for 3 weeks during which time it solidifies to a soft brown solid. Trituration of the solid with benzene affords yellow crystals, which are recrystallized from acetonitrite to give slightly yellow cubes of 3-{2-[4-(p-bromophenoxy)piperidyl]ethyl}-indole, m.p. 132°–134° C.

Calculated for $C_{21}H_{23}BrN_2O$: 63.16% C; 5.80% H; 7.07% N; 20.01% Br. Found: 63.05% C; 5.87% H/ 7.10% N; 19.85% Br.

EXAMPLE 8 a. A solution of 7.7 g of 1-benzyl-4-piperidinol in 25 ml. of dimethylformamide is added dropwise to a stirred suspension of 1.4 g of a 50% oil dispersion of sodium hydride in 75 ml. of dimethylformamide at 60°–70° C. Heating and stirring is continued until no more hydrogen gas is liberated, and then a solution of 7.7 g of fluorobenzene in 25 ml. of dimethylformamide is added. Heating and stirring are continued for 16 hours, the temperature is increased to 90°–95° C., and stirring is continued for 4 more hours. The reaction mixture is allowed to cool and is poured into 400 ml. of water. The aqueous solution is extracted with benzene, the benzene extracts are washed with water, dried, and the benzene is removed leaving an oil. The oil is fractionally distilled under reduced pressure and the fraction that boils at 135°–138° C/0.05mm is 1-benzyl-4-phenoxypiperidine.

b. By following the manipulative procedure described in Example 1(b), 1-benzyl-4-phenoxypiperidine is hydrogenated to give 4-phenoxypiperidine.

c. By following the manipulative procedure described in Example 5(c), 8.1 g of 4-phenoxypiperidine are reacted with 8.9 g of indole-3-glyoxyloyl chloride to give white needles, m.p. 205°–207° C., of 1-(indol-3-ylglyoxyloyl)-4-phenoxypiperidine.

d. By following the manipulative procedure described in Example 4(c), 5.0 g of 1-(indol-3-ylglyoxyloyl)-4-phenoxypiperidine are reacted with 2.8 g of lithium aluminum hydride to give white flakes of 3-[2-(4-phenoxypiperidyl)ethyl]indole, m.p. 123°–125° C.

Analysis: Calculated for $C_{21}H_{24}N_2O$: 78.71% C; 7.55% H; 8.74% N. Found: 78.90% C; 7.61% H; 8.92% N.

EXAMPLE 9 a. 86.4 g of 1-benzyl-4-piperidinol in 200 ml. and dimethylformamide are added dropwise to a stirred suspension of 34.7 g of a 50% oil dispersion of sodium hydride in 900 ml. of dimethylformamide at 60°–70° C. When no more hydrogen gas is liberated, a mixture of 68.4 g of p-difluorobenzene in 200 ml. of dimethylformamide is added slowly, and the temperature is raised to 80° C. Stirring and heating is continued for 48 hours, the reaction is cooled, poured into 2 l. of water, and the aqueous suspension is extracted with benzene. The benzene extracts are dried and the benzene is removed under reduced pressure, leaving a thick brown oil. The oil solidifies on standing. The solid is dissolved in 95% ethanol, the solution is filtered and the solvent is removed from the filtrate, leaving a yellow oil. The oil is dissolved in absolute ethanol, the solution is stirred, and saturated ethereal-HCl is added. A resultant hydrochloride salt precipitates out of solution and is collected and dried. The salt is recrystallized from an ethanol and ether mixture to give 1-benzyl-4-(p-fluorophenoxy)piperidine hydrochloride.

b. The 1-benzyl-4-(p-fluorophenoxy)piperidine hydrochloride is reduced to 4-(p-fluorophenoxy)piperidine following the manipulative procedure described in Example 1(b).

c. By following the manipulative procedure described in Example 4(b), 4-(p-fluorophenoxy)piperidine is reacted with indole-3-glyoxyloyl chloride to give 1-(indol-3-ylglyoxyloyl)-4-(p-fluorophenoxy)piperidine as an off-white solid. The solid is recrystallized twice from a methanol and water mixture to give white needles of the glyoxamide, m.p. 205°–207° C.

d. By following the manipulative procedure described in Example 2(d), 2.6 g of lithium aluminum hydride in 80 ml. of tetrahydrofuran and 6.0 g of 1-(indol-3-ylglyoxyloyl)-4-(p-fluorophenoxy)piperidine in 60 ml. of tetrahydrofuran are allowed to react to produce a white solid. The solid is recrystallized from isopropanol, and then from an ethanol and water mixture to give colorless cubes of 3-{2-[4-(p-fluorophenoxy)piperidyl]ethyl}indole, m.p. 109°–111° C.

Analysis: Calculated for $C_{21}H_{23}N_2FO$: 74.53% C; 6.85% H; 8.28% N. Found: 74.68% C; 6.79% H; 8.28% N.

EXAMPLE 10 a. 9.8 g of 2-methyl-indole-3-glyoxyloyl chloride are added portionwise to a stirred mixture of 9.0 g of 4-(p-fluorophenoxy)piperidine [Example 9(b)], 11.2 g of potassium carbonate, 45 ml. of chloroform and 45 ml. of water. The mixture is stirred for 16 hours and the resultant buff solid is collected, washed with ether and dried. The solid is recrystallized twice from an ethanol and water mixture to give 1-(2-methylindol-3-ylglyoxyloyl)-4-(p-fluorophenoxy)piperidine, m.p. 213°–214.5° C.

b. By following the manipulative procedure described in Example 2(d), 5.5 g of lithium aluminum hydride in 160 ml. of tetrahydrofuran and 12.0 g of 1-(2-methylindol-3-ylglyoxyloyl)-4-(p-fluorophenoxy)piperidine in 120 ml. of tetrahydrofuran are reacted to produce a white solid. The solid is recrystallized from an ethanol and water mixture (charcoal treatment) to give a white powder of 3-{2-[4-(p-fluorophenoxy)piperidyl]ethyl}-2-methylindole, m.p. 97°–99° C.

Analysis: Calculated for $C_{22}H_{25}FN_2O$: 74.96% C; 7.15% H; 7.95% N; 5.39% F. Found: 74.69% C; 7.20% H; 7.89% N; 5.29% F.

EXAMPLE 11 a. 13.9 g of oxalyl chloride are added dropwise to a stirred solution of 8.8 g of 5-methoxyindole in 160 ml. of ether at −10° C. After addition is complete, the reaction mixture is stirred for 10 minutes and the resultant orange solid is collected. The solid is washed with ether, and immediately suspended in a 100 ml. of ether. The ether suspension of 5-methoxy-indole-3-glyoxyloyl chloride is added slowly with cooling to a stirred mixture of 11.8 g of 4-(p-fluorophenoxy)piperidine [Example 9(b)] in 65 ml. of chloroform and 16.0 g of potassium carbonate in 65 ml. of water. The mixture is stirred overnight and then ether is added to the milky suspension. A white solid precipitates and is recrystallized from an ethanol and water mixture to give colorless needles, m.p. 176.5°–178° C., of 4-(p-fluorophenoxy)-1-(5-methoxyindol-3-ylglyoxyloyl)piperidine.

b. By following the manipulative procedure described in Example 2(d), 8.0 g of lithium aluminum hydride in 235 ml. of tetrahydrofuran and 18.0 g of 4-(p-fluorophenoxy)-1-(5-methoxyindol-3-ylglyoxyloyl)piperidine in 190 ml. of tetrahydrofuran are reacted to produce a white solid. The solid is recrystallized twice from 95% ethanol (charcoal treatment) to give white crystals of 3-{2-[4-(p-fluorophenoxy)piperidyl]ethyl}5-methoxyindole, m.p. 132°–134° C.

Analysis: Calculated for $C_{22}H_{25}FN_2O_2$: 71.71% C; 6.82% H; 7.58% N; 5.14% F. Found: 71.88% C; 6.99% H; 7.49% N; 4.80% F.

EXAMPLE 12 a. A mixture of 11.0 g of 4-(p-fluorophenoxy)-piperidine [Example 9(b)], 13.6 g of potassium carbonate, 60 ml. of chloroform and 60 ml. of water is stirred vigorously and 16.5 of 5-benzyloxy-indole-3-gloxyloyl chloride is added portionwise. The mixture is stirred overnight. A yellow oil separates, is removed from the supernatant liquid and stirred overnight with a mixture of 250 ml. of water and 100 ml. of hexane; a pale yellow solid results. The solid is collected and dried, and is recrystallized from ethanol and then from a methanol and water mixture to give a white powder m.p. 147.5°–149° C., of 1-(5-benzyloxyindol-3-ylglyoxyloyl)-4-(p-fluorophenoxy)-piperidine.

b. By following the manipulative procedure described in Example 2(d), 5.6 g of lithium aluminum hydride in 165 ml. of tetrahydrofuran and 15.2 g of 1-(5-benzyloxyindol-3-ylglyoxyloyl)-4-(p-fluorophenoxy)piperidine in 160 ml. of tetrahydrofuran are reacted to produce a white powder. The powder is recrystallized twice from an ethanol and water mixture and once from 95% ethanol (charcoal treatment) to give colorless needles of 5-benzyloxy-3-{2-[4-(p-fluorophenoxy)piperidyl]ethyl} indole, m.p. 134.5°–136.5° C.

Analysis: Calculated for $C_{28}H_{29}FN_2O_2$: 75.65% C; 6.57% H; 6.30% N. Found: 75.64% C; 6.71% H; 6.25% N.

EXAMPLE 13 a. A solution of 40.0 g of 1-benzyl-4-piperidinol in 75 ml. of dimethylformamide is added slowly to a stirred suspension of 6.7 g of a 50% oil dispersion of sodium hydride in 300 ml. of dimethylformamide at 60°–70° C. After addition is complete, heating is continued until no more hydrogen gas is liberated. A solution of 39.5 g of 1-fluoro-4-trifluoromethylbenzene in 50 ml. of dimethylformamide is added slowly while maintaining the reaction temperature at 60°–70° C. After addition is complete, stirring and heating at 70°–75° C. is continued for 16 hours. The mixture is poured into 1 l. of water and extracted with benzene. The combined benzene extracts are washed with water, dried, and solvent is removed under reduced pressure, leaving an oil. The oil is taken up in isopropanol and treated with ethereal-HCl, giving a white solid of 1-benzyl-4-(p-trifluoromethylphenoxy)piperidine hydrochloride.

b. A solution of 46.0 g of 1-benzyl-4-(p-trifluoromethylphenoxy)piperidine, the free base of Part (a), in 250 ml. of 95% ethanol is treated with 6.0 g of 10% palladium-on-charcoal catalyst and is shaken with hydrogen gas at 50° C. until the theoretical amount of hydrogen is absorbed. The suspension is cooled, filtered, and the solvent is removed. The residual oil is fractionally distilled under reduced pressure and the fraction which boils at 74°–76° C/0.05 mm is collected. The collected oil crystallizes on standing to give a solid of 4-(p-trifluoromethylphenoxy)piperidine.

c. 6.5 g of oxalyl chloride are added dropwise to a stirred solution of 8.8 g of 5,6-dimethoxy-2-methylindole in 160 ml. of ether at −10° C. After addition is complete, the mixture is stirred for 10 minutes and a bright orange precipitate of 5,6-dimethoxy-2-methylindole-3-glyoxyloyl chloride appears. The ether suspension of 5,6-dimethoxy-2-methyl-indole-3-glyoxyloyl chloride is added portion wise to a cooled stirring mixture of 12.3 g of 4-(p-trifluoromethylphenoxy)piperidine, 12.5 g of potassium carbonate, 50 ml. of chloroform and 60 ml. of water. The reaction mixture is stirred overnight and the resultant white solid is collected and dried. The solid is recrystallized twice from a methanol and water mixture to give 1-(5,6-dimethoxy-2-methylindol-3-ylglyoxyloyl)-4-(p-trifluoromethylphenoxy)piperidine m.p. 211°–213° C.

d. A suspension of 20.2 g of 1-(5,6-dimethoxy-2-methylindol-3-ylglyoxyloyl)-4-(p-trifluoromethylphenoxy)-piperidine in 175 ml. of tetrahydrofuran is added dropwise to a stirring suspension of 7.0 g of lithium aluminum hydride in 205 ml. of tetrahydrofuran. After addition is complete the reaction mixture is refluxed under nitrogen for 3 hours, cooled, and the excess hydride is carefully destroyed with water. The mixture is filtered, the filter cake is washed with tetrahydrofuran, and the tetrahydrofuran is removed under reduced pressure, leaving a brown, tacky solid. The solid is stirred vigorously in the presence of ether and a resulting white solid is collected and dried. The solid is recrystallized twice from an ethanol and water mixture to give white, feathery needles of 5,6-dimethoxy-2-methyl-3-{2-[4-(p-trifluoromethylphenoxy)piperidyl]ethyl} indole, m.p. 139°–141° C.

Analysis: Calculated for $C_{25}H_{29}F_3N_2O_3$: 64.92% C; 6.32% H; 6.06% N; 12.32% F. Found: 64.95% C; 6.40% H; 5.98% N; 11.97% F.

EXAMPLE 14 a. A solution of 11.0 g of 4-(p-trifluoromethylphenoxy)piperidine [Example 13(b)], in 45 ml. of chloroform is added to a solution of 11.2 g of potassium carbonate in 45 ml. of water. The mixture is stirred vigorously and 9.4 g of indole-3-glyoxyloyl chloride are added portionwise. About 5 minutes after addition is complete, a white solid precipitates from the solution. The reaction mixture is stirred for 30 minutes and the solid is collected, washed well with absolute ether, and dried. The solid is recrystallized from an ethanol-water mixture to give white needles, m.p. 200.5°–202° C., of 1-(indol-3-ylglyoxyloyl)-4-(p-trifluoromethylphenoxy)piperidine.

b. A solution of 13.6 g of 1-(indol-3-ylgloxyloyl)-4-(p-trifluoromethylphenoxy)piperidine is added dropwise to a stirred suspension of 6.1 g of lithium aluminum hydride in 160 ml. of tetrahydrofuran. The mixture is stirred and refluxed under nitrogen for 3 hours. The mixture is cooled, the excess hydride is destroyed carefully with water, the mixture is filtered, and the filter cake is washed well with tetrahydrofuran. The tetrahydrofuran is removed under reduced pressure, leaving a yellow solid. The solid is recrystallized from an ethanol and water mixture, cyclohexane, and cyclohexane with charcoal to give off-white flakes, m.p. 130°–132° C., of 3-{2-]4-(p-trifluoromethylphenoxy)-piperidyl]ethyl} indole.

Analysis: Calculated for $C_{22}H_{23}F_3N_2O$: 68.02% C; 5.96% H/ 7.21% N. Found: 67.92% C; 5.95% H; 7.19% N.

EXAMPLE 15 a. A solution of 11.2 g of p-fluorophenol in 25 ml. of dimethylformamide is added dropwise to a stirred suspension of 7.4 g of a 50% oil dispersion of sodium hydride in 100 ml. of dimethylformamide. After no more hydrogen gas is liberated, 31.7 g of 1-benzhydryl-3-methanesulfonatoazetidine in 50 ml. of dimethylformamide are added dropwise. The solution is stirred at 55°–60° C. for 48 hours and the resultant dark brown solution is poured into 500 ml. of ice and water, depositing a thick dark brown oil. The supernatant aqueous solution is decanted and the oil is taken up in ether. The aqueous solution is extracted with ether and the ether solutions are combined. The combined ether solution is dried, and the ether is removed under reduced pressure, leaving a brown oil. The oil is triturated with hot hexane, the supernatant hexane is decanted from the insoluble oil and the hexane is removed under reduced pressure, leaving an orange oil. This operation is repeated several times, and the resulting oil solidifies to an orange solid. The solid is chilled in a dry ice and isopropanol bath and triturated with isopropyl ether, causing a light beige solid to separate. The solid is collected, washed with petroleum ether and dried. The solid is recrystallized from an ethanol-water mixture to give a white crystalline solid of 1-benzyhydryl-3-(p-fluorophenoxy)-azetidine.

b. A solution of 20.0 g of 1-benzhydryl-3-(4-fluorophenoxy)azetidine and 10.3 g of phenylchloroformate in 200 ml. of toluene is refluxed for 16 hours. The reaction mixture is cooled, and the toluene is removed under reduced pressure to give a yellow oil. The oil is triturated with hexane to give a white solid of 1-phenoxycarbonyl-3-(p-fluorophenoxy)azetidine.

c. A sample of 12.0 g of 1-phenoxycarbonyl-3-(p-fluorophenoxy)azetidine is dissolved in 160 ml. of ethanol and 100 ml. of 45% KOH added, and the solution is stirred and refluxed under nitrogen for 15 hours. After cooling, most of the ethanol is removed under reduced pressure and the resultant oily dispersion is extracted with ether. The ether phase is extracted with 3N HCl, the acid extract is basified with 6N NaOH, and the basic solution is extracted with benzene. The benzene is dried and removed under reduced pressure to give a yellow oil. The oil is dissolved in ether and ethreal-HCl is added. The resulting solid is collected and recrystallized from an acetone and ether mixture to give 3-(p-fluorophenoxy)-azetidine hydrochloride.

d. A mixture of 1.5 g of 3-(p-fluorophenoxy)-azetidine, 1.9 g of potassium carbonate, 15 ml. of chloroform and 15 ml. of water is stirred vigorously and 1.7 g of indole3-glyoxyloyl chloride are added portionwise. A white oily suspension is formed which, when diluted with ether gives a white solid. The solid is recrystallized from a dimethylformamide and water mixture to give a white solid, m.p. 247°–249°, of 1-(indol-3-ylglyoxyloyl)-3-(p-fluorophenoxy)azetidine.

e. By following the manipulative procedure described in Example 2(d), 0.7 g of lithium aluminum hydride in 30 ml. of tetrahydrofuran and 1.5 g of 1-(indol-3-ylglyoxyloyl)-3-(p-fluorophenoxy)azetidine in 30 ml. of tetrahydrofuran are reacted to produce a white solid. The solid is recrystallized twice from an ethanol and water mixture to give colorless needles of 3-{2-[3-(p-fluorophenoxy)azetidinyl]ethyl}indole, m.p. 111°–113°.

Analysis: Calculated for $C_{19}H_{19}FN_2O$: 73.35% C; 6.15% H; 9.00% N; 6.10% F. Found: 73.38% C; 6.34% H; 9.01% N; 5.92% F.

EXAMPLE 16 a. 7.7 g of 5-bromo-indole-3-glyoxyloyl chloride are added, portionwise, to a stirred mixture of 5.7 g of 4-(p-fluorophenoxy)piperidine, Example 9(b), in 25 ml. of chloroform and 7.6 g of potassium carbonate in 25 ml. of water. The mixture is stirred overnight, the chloroform layer is separated, and the chloroform is removed under reduced pressure to give an off-white solid. The solid is recrystallized from an ethanol and water mixture to give colorless needles, m.p. 187°–189° C., of 5-bromo-1-(indol-3-ylglyoxyloyl)-4-(p-fluorophenoxy)piperidine.

b. 10.0 g of 5-bromo-1-(indol-3-ylglyoxyloyl)-4-(p-fluorophenoxy)piperidine in 100 ml. of tetrahydrofuran are added dropwise to a stirred suspension of 4.2 g of lithium aluminum hydride in 115 ml. of tetrahydrofuran. The mixture is stirred and refluxed under nitrogen for 3 hours, cooled, and 17 ml. of water are added dropwise. The mixture is filtered, the filter cake is washed well with tetrahydrofuran, and the solvent is removed under reduced pressure to give a glassy oil. The oil is rubbed with a glass rod in the presence of hexane to give a white solid. The solid is recrystallized three times from an ethanol and water mixture with charcoal to give colorless cubes, m.p. 104°–106° C., of 5-bromo-3-{2-[4-(pfluorophenoxy)piperidyl]ethyl}indole.

Analysis: Calculated for $C_{21}H_{22}BrFN_2O$: 60.43% C; 5.31% H; 6.71% N. Found: 61.10% C; 5.34% H; 6.71% N.

EXAMPLE 17 a. A solution of 10.0 g of 1-benzyl-4-phenyl-4-piperidinol in dimethylformamide is added slowly to a stirred suspension of 1.7 g of a 57% oil dispersion of sodium hydride in 70 ml. of dimethylformamide at 60°–70° C. After addition is complete, heating is continued until no more hydrogen gas is liberated. A solution of 6.3 g of p-fluorobenzotrifluoride in 15 ml. of dimethylformamide is added dropwise. After addition is complete, stirring and heating at 80°–82° C. is continued for 72 hours. The mixture is poured into 200 ml. of water, extracted with benzene, the combined benzene extracts are washed with water, dried, and the solvent is removed under reduced pressure leaving an orange solid. The solid, which is a mixture of the desired product and starting material, is triturated with absolute ethanol, and this effectively removes the starting material, leaving the desired piperidine as a white solid. The solid is recrystallized from ethanol to give colorless needles of 1-benzyl-4-phenyl-4-(p-trifluoromethylphenoxy)piperidine.

b. A solution of 10.0 g of 1-benzyl-4-phenyl-4-(p-trifluoromethylphenoxy)piperidine and 4.1 g of phenylchloroformate in 100 ml. of toluene was refluxed for 17 hours. The toluene was removed under reduced pressure to give a colorless oil which when rubbed with a glass rod in the presence of hexane gave a white solid of 1-phenoxycarbonyl-4-phenyl-4-(p-trifluoromethylphenoxy)piperidine.

c. A sample of 7.4 g of 1-phenoxycarbonyl-4-phenyl-4-(p-trifluoromethylphenoxy)piperidine is dissolved in 70 ml. of ethanol and 48 ml. of 45% aqueous KOH added, and the solution is stirred and refluxed under nitrogen for 4 hours. After cooling most of the ethanol is removed under reduced pressure and the resultant oily dispersion is extracted with ether. The ether was dried and then evaporated under reduced pressure to give a waxy, white solid of 4-phenyl-4(p-trifluoromethylphenoxy)piperidine.

d. A mixture of 4.2 g of 4-phenyl-4-(p-trifluoromethylphenoxy)piperidine, 1.9 g of potassium carbonate and 2.7 g of 3-(2-bromoethyl)indole in 50 ml. of dimethylformamide is stirred and heated at 50° C. for 16 hours. After cooling, 100 ml. of water are added dropwise, precipitating a yellow solid. The solid is triturated with hexane and then twice recrystallized from acetonitrile to colorless crystals of 3-{2-[4-phenyl-4-(p-trifluoromethylphenoxy)piperidyl]ethyl}indole, m.p. 135°–136° C.

Analysis: Calculated for $C_{28}H_{27}F_3N_2O$: 72.39% C; 5.85% H; 6.03% N. Found: 72.64% C; 5.80% H; 5.93% N.

We claim:

1. A method of treating pain and reducing blood pressure which comprises administering to a patient in pain or having elevated blood pressure an effective amount of a compound of the formula:

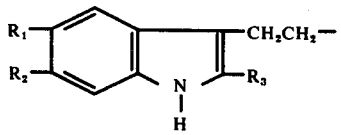

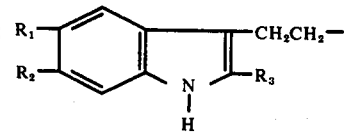

in which $R_1$ and $R_2$ are hydrogen, halogen, alkyl of from 1 to 2 carbon atoms, alkoxy of from 1 to 2 carbon atoms or phenalkoxy of from 7 to 9 carbon atoms; $R_3$ is hydrogen or alkyl of from 1 to 3 carbon atoms; $R_4$ is hydrogen or phenyl; $R_5$ is halogen, alkyl of from 1 to 4 carbon atoms, alkoxy of from 1 to 2 carbon atoms, nitro or trifluoromethyl; $m$ is an integer from 1 to 3; $n$ is 1 or 2; and $q$ is 0, 1 or 2; or a physiologically tolerable acid addition salt thereof.

2. The method defined in claim 1 in which $R_1$ and $R_2$ are hydrogen, bromine, methoxy or benzyloxy, $R_3$ is hydrogen or methyl, $R_5$ is methyl, fluorine, chlorine, bromine or trifluoromethyl, and $q$ is 0 or 1.

3. The method defined in claim 1 in which the active compound is 3-{2-[4-(p-tolyloxy)piperidyl]ethyl} indole or a physiologically tolerable acid addition salt thereof.

4. The method defined in claim 1 in which the active compound is 3-{2-[4-(p-bromophenoxy)piperidyl]ethyl} indole or a physiologically tolerable acid addition salt thereof.

5. The method defined in claim 1 in which the active compound is 5,6-dimethoxy-2-methyl-3-{2-[4-(p-trifluoromethylphenoxy)piperidyl]ethyl} indole or a physiologically tolerable acid addition salt thereof.

6. The method defined in claim 1 in which the active compound is 3-{2-[4-(p-chlorophenoxy)piperidyl]ethyl} indole or a physiologically tolerable acid addition salt thereof.

7. The method defined in claim 1 in which the active compound is 3-{2-[4-(p-fluorophenoxy)piperidyl]ethyl} indole or a physiologically tolerable acid addition salt thereof.

8. The method defined in claim 1 in which the active compound is 3-[2-(4-phenoxypiperidyl)ethyl]indole or a physiologically tolerable acid addition salt thereof.

9. The method defined in claim 1 in which the active compound is a compound of the formula:

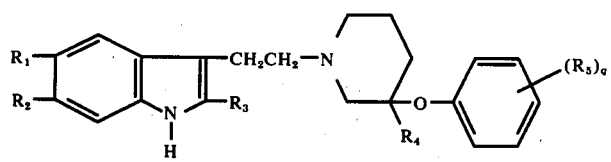

in which $R_1$ and $R_2$ are hydrogen, bromine, methoxy or benzyloxy, $R_3$ is hydrogen or methyl, $R_5$ is methyl, fluorine, chlorine, bromine or trifluoromethyl, and $q$ is 0 or 1.

10. The method defined in claim 1 in which the active compound is 3-{2-[3-(p-tolyloxypiperidyl]ethyl} indole or a physiologically tolerable acid addition salt thereof.

11. The method defined in claim 1 in which the active compound is a compound of the formula:

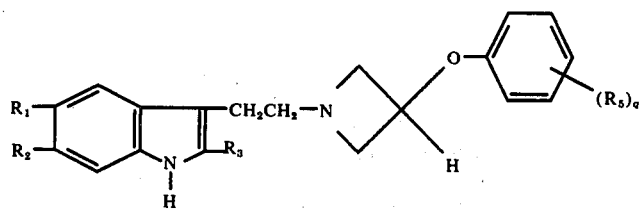

in which $R_1$ and $R_2$ are hydrogen, bromine, methoxy or benzyloxy, $R_3$ is hydrogen or methyl, $R_5$ is methyl, fluorine, chlorine, bromine or trifluoromethyl, and $q$ is 0 or 1.

12. The method defined in claim 1 in which the active compound is 3-{2-[3-(p-fluorophenoxy)azetidinyl]-ethyl} indole or a physiologically tolerable acid addition salt thereof.

13. A method of treating pain which comprises administering to a patient in pain an effective amount of a compound of the formula:

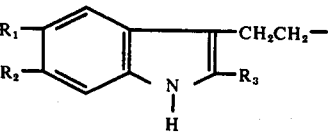

in which $R_1$ and $R_2$ are hydrogen, halogen, alkyl of from 1 to 2 carbon atoms, alkoxy of from 1 to 2 carbon atoms or phenalkoxy of from 7 to 9 carbon atoms; $R_3$ is hydrogen or alkyl of from 1 to 3 carbon atoms; $R_4$ is hydrogen or phenyl; $R_5$ is halogen, alkyl of from 1 to 4 carbon atoms, alkoxy of from 1 to 2 carbon atoms, nitro or trifluoromethyl; $m$ is an integer from 1 to 3; $n$ is 1 or 2; and $q$ is 0, 1 or 2; or a physiologically tolerable acid addition salt thereof.

14. The method defined in claim 13 in which $R_1$ and $R_2$ are hydrogen, bromine, methoxy or benzyloxy, $R_3$ is hydrogen or methyl, $R_5$ is methyl, fluorine, chlorine, bromine or trifluoromethyl, and $q$ is 0 or 1.

15. The method defined in claim 13 in which the active compound is 3-{2-[4-(p-tolyloxy)piperidyl]ethyl}indole or a physiologically tolerable acid addition salt thereof.

16. The method defined in claim 13 in which the active compound is 3-{2-[4-(p-bromophenoxy)piperidyl]ethyl}indole or a physiologically tolerable acid addition salt thereof.

17. The method defined in claim 13 in which the active compound is 5,6-dimethoxy-2-methyl-3-{2-[4-(p-trifluoromethylphenoxy)piperidyl]ethyl}indole or a physiologically tolerable acid addition salt thereof.

18. The method defined in claim 13 in which the active compound is 3-{2-[4-(p-chlorophenoxy)piperidyl]ethyl}indole or a physiologically tolerable acid addition salt thereof.

19. The method defined in claim 13 in which the active compound is 3-{2-[4-(p-fluorophenoxy)piperidyl]ethyl}indole or a physiologically tolerable acid addition salt thereof.

20. The method defined in claim 13 in which the active compound is 3-[2-(4-phenoxypiperidyl)ethyl]indole or a physiologically tolerable acid addition salt thereof.

21. The method defined in claim 13 in which the active compound is a compound of the formula:

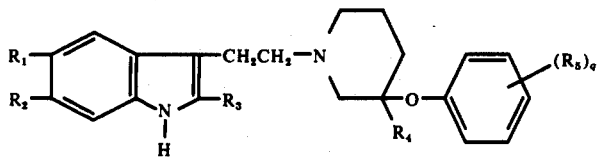

in which $R_1$ and $R_2$ are hydrogen, bromine, methoxy or benzyloxy, $R_3$ is hydrogen or methyl, $R_5$ is methyl, fluorine, chlorine, bromine or trifluoromethyl, and $q$ is 0 or 1.

22. The method defined in claim 13 in which the active compound is 3-{2-[3-(p-tolyloxypiperidyl)ethyl}indole or a physiologically tolerable acid addition salt thereof.

23. The method defined in claim 13 in which the active compound is a compound of the formula:

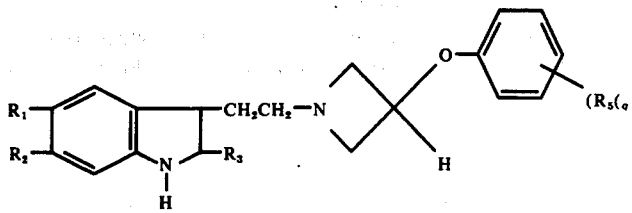

in which $R_1$ and $R_2$ are hydrogen, bromine, methoxy or benzyloxy, $R_3$ is hydrogen or methyl, $R_5$ is methyl, fluorine, chlorine, bromine or trifluoromethyl, and $q$ is 0 or 1.

24. The method defined in claim 13 in which the active compound is 3-{2-[3-(p-fluorophenoxy)azetidinyl]-ethyl}indole or a physiologically tolerable acid addition salt thereof.

25. A method of reducing blood pressure which comprises administering to a patient having elevated blood pressure an effective amount of a compound of the formula:

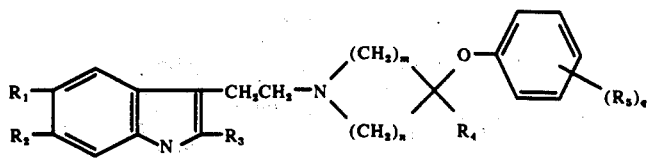

in which $R_1$ and $R_2$ are hydrogen, halogen, alkyl of from 1 to 2 carbon atoms, alkoxy of from 1 to 2 carbon atoms or phenalkoxy of from 7 to 9 carbon atoms; $R_3$ is hydrogen or alkyl of from 1 to 3 carbon atoms; $R_4$ is hydrogen or phenyl; $R_5$ is halogen, alkyl of from 1 to 4 carbon atoms, alkoxy of from 1 to 2 carbon atoms, nitro or trifluoromethyl; $m$ is an integer from 1 to 3; $n$ is 1 or 2; and $q$ is 0, 1 or 2; or a physiologically tolerable acid addition salt thereof.

26. The method defined in claim 25 in which $R_1$ and $R_2$ are hydrogen, bromine, methoxy or benzyloxy, $R_3$ is hydrogen or methyl, $R_5$ is methyl, fluorine, chlorine, bromine or trifluoromethyl, and $q$ is 0 or 1.

27. The method defined in claim 25 in which the active compound is 3-{2-[4(p-tolyloxy)piperidyl]ethyl}indole or a physiologically tolerable acid addition salt thereof.

28. The method defined in claim 25 in which the active compound is 3-{2-[4-(p-bromophenoxy)-piperidyl]ethyl}indole or a physiologically tolerable acid addition salt thereof.

29. The method defined in claim 25 in which the active compound is 5,6-dimethoxy-2-methyl-3-{2-[4-

(p-trifluoromethylphenoxy)piperidyl]ethyl}indole or a physiologically tolerable acid addition salt thereof.

30. The method defined in claim 25 in which the active compound is 3-{2-[4-(p-chlorophenoxy)-piperidyl]ethyl}indole or a physiologically tolerable acid addition salt thereof.

31. The method defined in claim 25 in which the active compound is 3-{2-[4-(p-fluorophenoxy)-piperidyl]ethyl}indole or a physiologically tolerable acid addition salt thereof.

32. The method defined in claim 25 in which the active compound is 3-[2-(4-phenoxypiperidyl)ethyl]indole or a physiologically tolerable acid addition salt thereof.

33. The method defined in claim 25 in which the active compound is a compound of the formula:

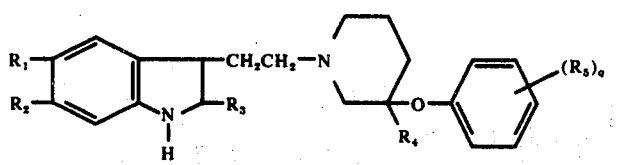

in which $R_1$ and $R_2$ are hydrogen, bromine, methoxy or benzyloxy, $R_3$ is hydrogen or methyl, $R_5$ is methyl, fluorine, chlorine, bromine or trifluoromethyl, and $q$ is 0 or 1.

34. The method defined in claim 25 in which the active compound is 3-{2-[3-(p-tolyloxypiperidyl]ethyl}indole or a physiologically tolerable acid addition salt thereof.

35. The method defined in claim 25 in which the active compound is a compound of the formula:

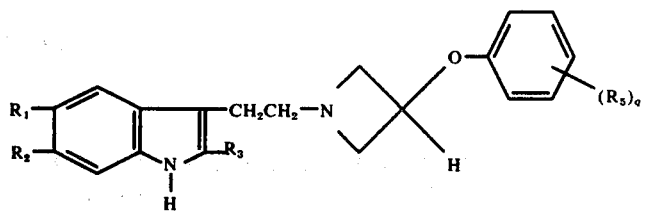

in which $R_1$ and $R_2$ are hydrogen, bromine, methoxy or benzyloxy, $R_3$ is hydrogen or methyl, $R_5$ is methyl, fluorine, chlorine, bromine or trifluoromethyl, and $q$ is 0 or 1.

36. The method defined in claim 25 in which the active compound is 3-{2-[3-(p-fluorophenoxy)azetidinyl]-ethyl}indole or a physiologically tolerable acid addition salt thereof.

* * * * *

UNITED STATES PATENT AND TRADEMARK OFFICE
CERTIFICATE OF CORRECTION

PATENT NO. : 4,031,221

DATED : June 21, 1977

INVENTOR(S) : Grover C. Helsley et al.

It is certified that error appears in the above-identified patent and that said Letters Patent are hereby corrected as shown below:

Column 3, line 7, "...piperidyl[ethyl..." should be
--...piperidyl]ethyl...--;

line 50, "...piperidyl)ethyl]ethyl]indole" should be
--...piperidyl)ethyl]indole--;

Column 4, line 38, "700 ml" should be --70 ml--;

Column 6, line 15, "...-3ylglyoxyloyl..." should be
--...-3-ylglyoxyloyl...--;

Column 12, line 48, "2-]4-(p-..." should be --2-[4-(p-...--;

Column 13, line 37, "indole3-glyoxyloyl" should be --indole-3-glyoxyloyl--;

Column 14, line 14, "...4-(pfluoro..." should be --...4-(p-fluoro...--;

line 57, "...4(p-trifluoro..." should be --...4-(p-trifluoro...--;

UNITED STATES PATENT AND TRADEMARK OFFICE
CERTIFICATE OF CORRECTION

PATENT NO. : 4,031,221
DATED : June 21, 1977
INVENTOR(S) : Grover C. Helsley et al.

It is certified that error appears in the above–identified patent and that said Letters Patent are hereby corrected as shown below:

Column 18, line 5, in the structural formula of claim 23, the substituent "$(R_5(_q$" should be --$(R_5)_q$--.

Signed and Sealed this

Sixth Day of December 1977

[SEAL]

Attest:

RUTH C. MASON
Attesting Officer

LUTRELLE F. PARKER
Acting Commissioner of Patents and Trademarks